US008225669B2

(12) United States Patent
Pierson

(10) Patent No.: US 8,225,669 B2
(45) Date of Patent: Jul. 24, 2012

(54) IMMERSED PROBE OVER PRESSURIZED ELASTOMER

(75) Inventor: Eric Pierson, Bozeman, MT (US)

(73) Assignee: New Gate Technologies, Bozeman, MT (US)

( * ) Notice: Subject to any disclaimer, the term of this patent is extended or adjusted under 35 U.S.C. 154(b) by 938 days.

(21) Appl. No.: 12/113,695

(22) Filed: May 1, 2008

(65) Prior Publication Data
US 2008/0276710 A1 Nov. 13, 2008

Related U.S. Application Data

(60) Provisional application No. 60/916,451, filed on May 7, 2007.

(51) Int. Cl.
*G01N 29/28* (2006.01)
*G01N 29/265* (2006.01)

(52) U.S. Cl. ........................................................ 73/644

(58) Field of Classification Search .................... 73/643, 73/644, 635, 636, 639
See application file for complete search history.

(56) References Cited

U.S. PATENT DOCUMENTS

| 2,532,507 | A | * | 12/1950 | Meunier | 310/336 |
| 2,545,101 | A | * | 3/1951 | Meunier | 310/336 |
| 2,992,553 | A | * | 7/1961 | Joy | 73/636 |
| 3,251,220 | A | * | 5/1966 | Joy | 73/614 |
| 3,730,121 | A | * | 5/1973 | Supernaw | 114/20.1 |
| 3,798,961 | A | * | 3/1974 | Flambard et al. | 73/644 |
| 4,059,098 | A | * | 11/1977 | Murdock | 600/437 |
| 4,237,901 | A | * | 12/1980 | Taenzer | 600/443 |
| H1290 | H | * | 2/1994 | Mann et al. | |
| 5,419,195 | A | * | 5/1995 | Quinn | 73/623 |
| 5,585,565 | A | * | 12/1996 | Glascock et al. | 73/644 |
| 7,481,115 | B2 | * | 1/2009 | Hasegawa et al. | 73/644 |
| 7,614,304 | B2 | * | 11/2009 | Gunasekaran et al. | 73/598 |

* cited by examiner

*Primary Examiner* — Hezron E Williams
*Assistant Examiner* — Rose M Miller
(74) *Attorney, Agent, or Firm* — McKee, Voorhees & Sease, P.L.C.

(57) ABSTRACT

A method for ultrasonic testing includes placing an ultrasonic probe in a liquid bath inside of a pressure vessel having an elastomeric diaphragm stretched across an opening of the pressure vessel, applying pressure within the pressure vessel to bring the elastomeric diaphragm towards a test piece, and conducting ultrasonic testing of the test piece using the ultrasonic probe. A device for ultrasonic testing of a test piece includes a pressure vessel having an elastomeric diaphragm and an ultrasonic probe disposed within the pressure vessel.

23 Claims, 25 Drawing Sheets

IMMERSED PROBE OVER PRESSURIZED ELASTOMER

CROSS-REFERENCE TO RELATED APPLICATIONS

This application claims priority under 35 U.S.C. §119(e) to provisional application Ser. No. 60/916,451 filed May 7, 2007, herein incorporated by reference in its entirety.

BACKGROUND OF THE INVENTION

The present invention relates to ultrasonic testing. Ultrasonic testing generally involves very short ultrasonic pulse-waves which are launched into materials to detect internal flaws or to determine the material type or characteristics of material. The nature of an ultrasound test requires that the ultrasonic probe come into complete contact with the surface of the test piece. The reason for this is that air between the probe and the test piece will give inconsistent and incorrect results in the test. Because the high frequency sound waves from the probe must travel into the test piece consistently across the entire test area there must not be any voids (air gaps) between the probe and the test piece. The very nature of an ultrasound test is to find unwanted voids in the test piece, without complete coupling between the test piece and the probe the test is of no use.

There are two primary methods of ensuring that the coupling between the probe 18 and the test piece are consistent. First, as shown in FIG. 1, coupling between the probe 18 and the piece 14 with a gel 16 and significant down-force of 30-40 PSI may be used. Second, as shown in FIG. 2, the test piece 14 and probe 18 may be immersed in a liquid bath 20. While both of these methods are very effective in many applications they are not generally effective in high volume production, or with delicate test pieces or parts that are non-immersible.

Other challenges arise when the test piece is large enough to require that the probe be moved to test the entire surface. Because the probe must remain in intimate contact with the surface of the test piece motion of the probe across the surface of the test piece becomes very difficult. The coupling mechanism (gel or elastomeric couplant) can be worn out or will not maintain a consistent coupling with the test piece. The combination of high down force and high friction makes moving the probe while scanning ineffective. The probe can be moved over the test piece in immersion applications (because it is not touching the piece) however that is not of any use in non-immersion applications.

Due to problems such as the test pieces in question being fragile, non-immersible and having non-uniform surfaces, ultrasonic testing has significant limitation. What is needed is a way to overcome these and other problems.

BRIEF SUMMARY OF THE INVENTION

Therefore, it is a primary object, feature, or advantage of the present invention to improve over the state of the art.

It is a further object, feature, or advantage of the present invention to provide for ultrasonic testing which does not require the test piece to come in contact with liquids.

A still further object, feature, or advantage of the present invention is to provide for ultrasonic testing which provides consistent coupling with all irregular surfaces.

Another object, feature, or advantage of the present invention is to provide for ultrasonic testing that does not require applying high concentrated forces to delicate surfaces.

Yet another object, feature, or advantage of the present invention is to provide for ultrasonic testing that allows the probe to be moved over the surface with little effort while maintaining the coupling to the test piece at all times.

One or more of these and/or other objects, features, or advantages of the present invention will become apparent from the specification and claims that follow.

According to one aspect of the present invention, a method for ultrasonic testing is provided. The method includes placing an ultrasonic probe in a liquid bath inside of a pressure vessel having an elastomeric diaphragm stretched across an opening of the pressure vessel and applying pressure within the pressure vessel to bring the elastomeric diagram towards a test piece. Ultrasonic testing of the test piece is then conducted using the ultrasonic probe. The pressure vessel may be a bell-jar. The test piece may be a catalyst substrate.

According to another aspect of the present invention, an apparatus for ultrasonic testing of a test piece is provided. The apparatus includes a pressure vessel having an elastomeric diaphragm and an ultrasonic probe disposed within the pressure vessel. There is a liquid bath within the pressure vessel. There may be a drive shaft operatively connected to the pressure vessel for rotating, translating, or otherwise actuating movement of the ultrasonic probe. There may be a mechanism for holding the ultrasonic probe in a static location.

DETAILED DESCRIPTION OF THE PREFERRED EMBODIMENT

The present invention includes a method for ultrasonic testing that addresses problems with conventional ultrasonic testing. This invention allows for the probe to be immersed while the part remains dry. An ultrasonic probe is suspended in a liquid bath inside of a bell-jar with an elastomeric diaphragm stretched across the bottom of the bell-jar. The liquid on the probe side of the elastomeric diaphragm provides consistent coupling with the test piece on the other side of the elastomer. By applying pressure inside of the bell-jar the elastomer is forced down against the test piece surface conforming to the irregularities in the surface and providing intimate contact at all points. The liquid bath in which the probe resides allows the probe to be moved effortlessly across the surface of the part with no unwanted forces applied to the test piece surface. Under very light pressure the elastomeric diaphragm only applies a very slight pressure to the delicate face of the test piece while maintaining the intimate contact required to ensure a consistent ultrasonic test.

The following diagrams depict the invention as used to inspect for internal cracking in automotive and diesel catalyst substrate. These substrates are made of ceramic or silicon carbide and are susceptible to internal cracking during manufacturing. The challenges in ultrasonically testing these pieces are due to the fragile nature of the parts, their inability to be immersed, their size and their typically irregular surfaces. Test results from ultrasonic testing may be used to characterize a test piece, identify flaws or defects in the test piece, reject test pieces, identify the absence of flaws or defects in a test or their other purposes. Of course, the present invention may be used in other contexts for testing of other types of test pieces, especially those which involve test pieces which are fragile in nature, have an inability to be immersed, and have irregular surfaces.

Figure 1:
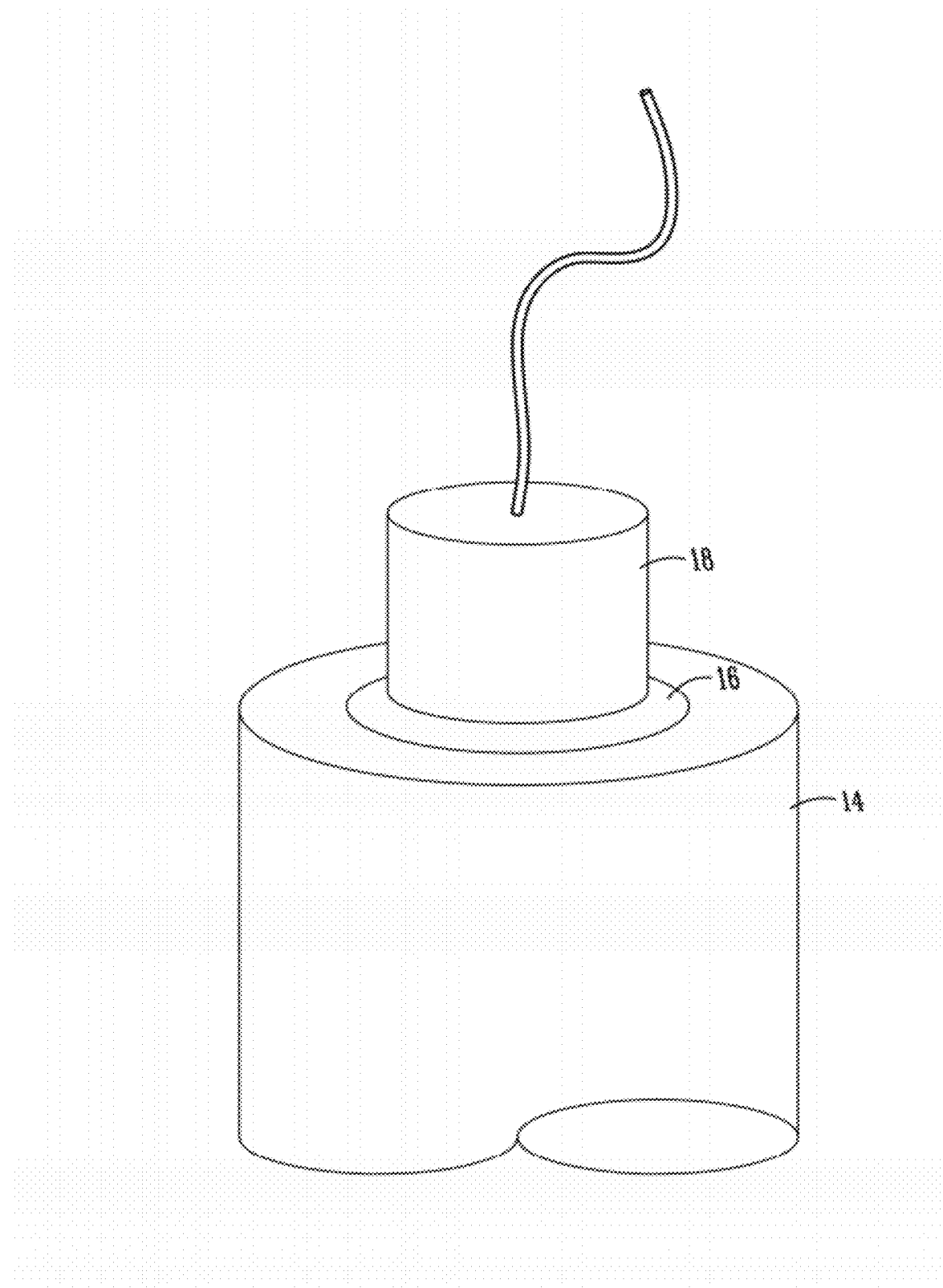
FIG. 1 illustrates a prior art method of ultrasonic testing where a gel couplet is used.
Figure 2:
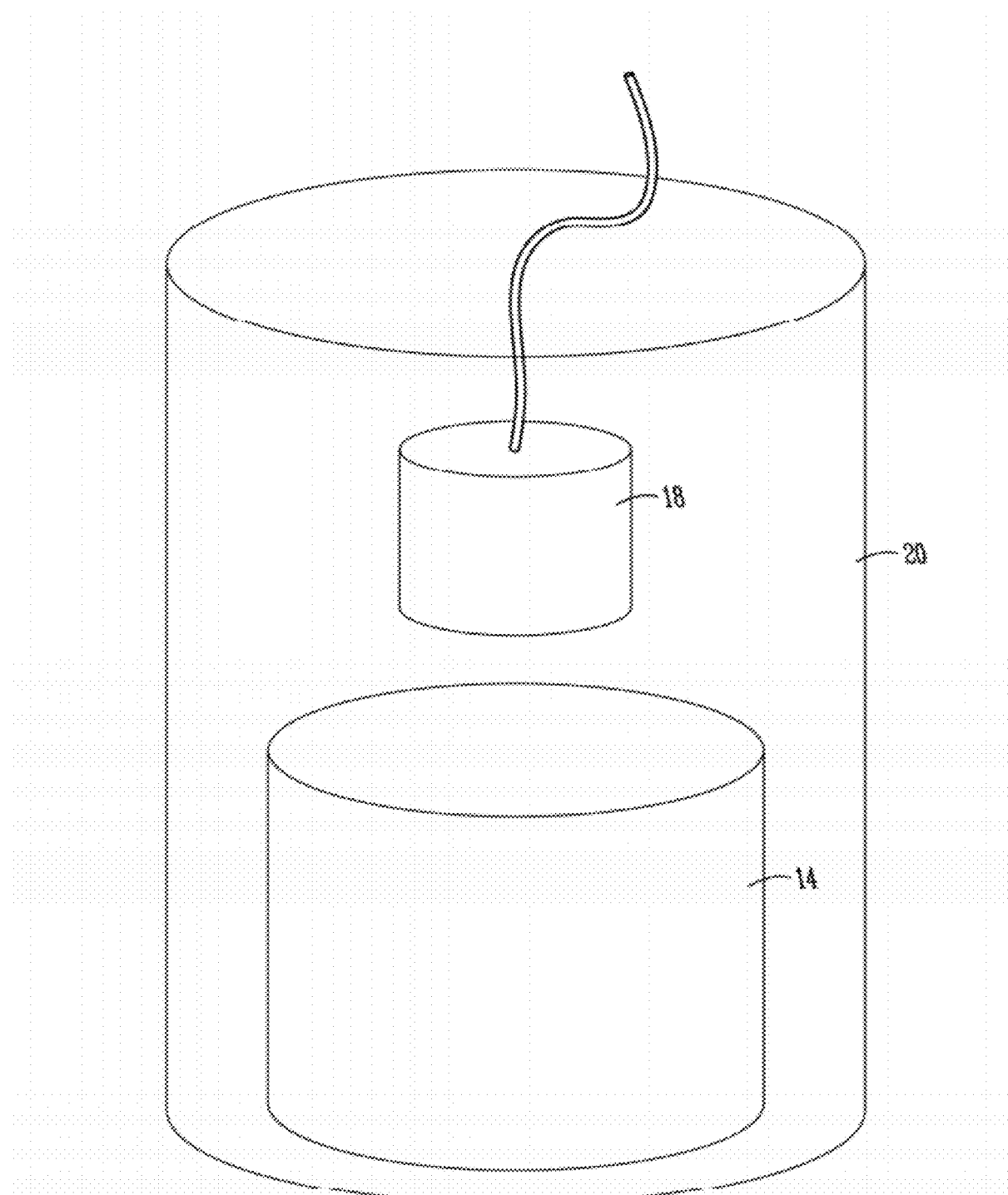
FIG. 2 illustrates a prior art method of ultrasonic testing where a test piece is placed in an immersion tank.
Figure 3:
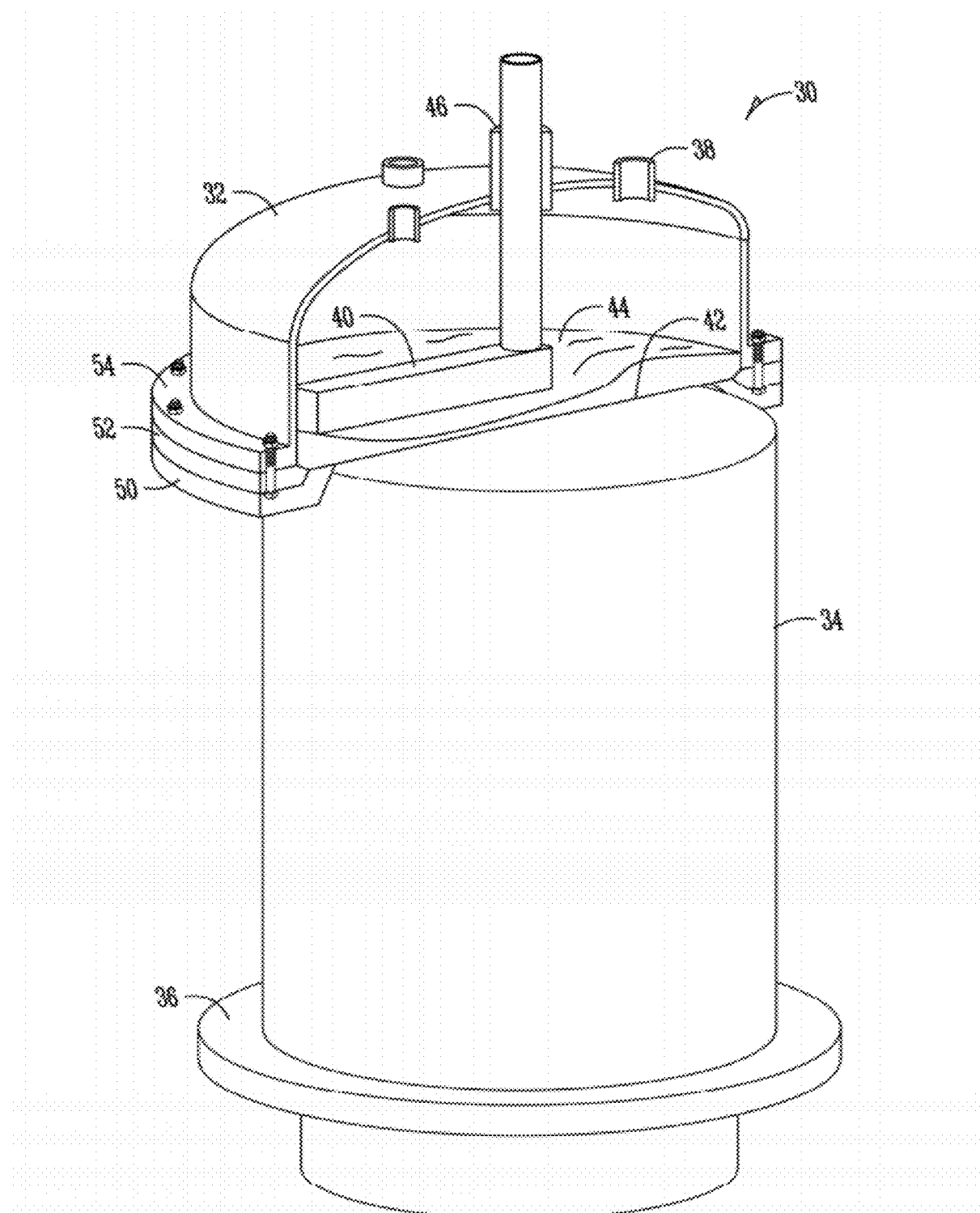
FIG. 3 is a perspective view of an ultrasound bell jar assembly according to one embodiment of the present invention.

FIG. 3 illustrates one embodiment of a bell-jar assembly applied to an test object. The system 30 illustrates an ultrasound bell-jar assembly 32 proximate a test object 34. Here, the test object 34 is a catalyst substrate. A substrate lift platform 36 is also shown for lifting the substrate 34 to the ultrasound bell-jar assembly 32. The substrate lift platform 36 allows non-identical test objects to be used in the same setup. FIG. 3 shows the system with a part in testing. The bell-jar assembly 32 houses the probe and sits above the test piece 34. The test piece 34 is placed on a stable lift platform 36 which lifts it into the diaphragm of the bell-jar assembly 32. Once the part is lifted into the diaphragm, pressure is applied inside the bell jar to force the diaphragm into the face of the test piece.

Figure 4:
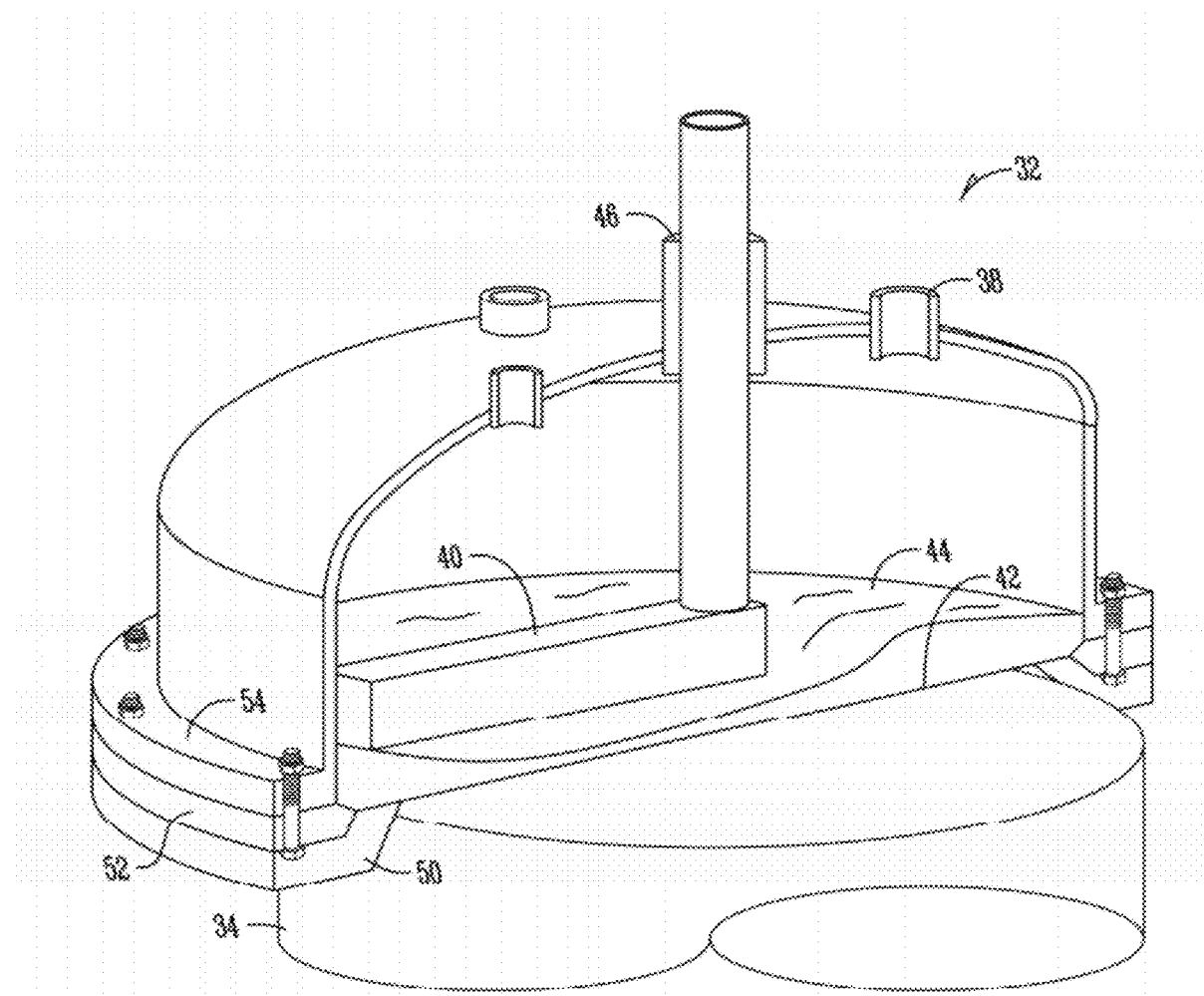
FIG. 4 is a sectional perspective view of a portion of the ultrasound bell jar assembly.

FIG. 4 illustrates another view of the ultrasound bell-jar assembly 32 where compressed air, which can be as low as one PSI, is received through an inlet 38. A probe 40 within the ultrasound bell-jar assembly 32. The probe 40 is placed proximate or adjacent an elastomeric diaphragm 42. There is a liquid bath 44 within the ultrasound bell-jar assembly 32. There is also a probe feed-through opening 46 to allow for electrical connections to the probe 40 to be pass into the ultrasound bell-jar assembly 32 while maintaining pressure.

Figure 5:
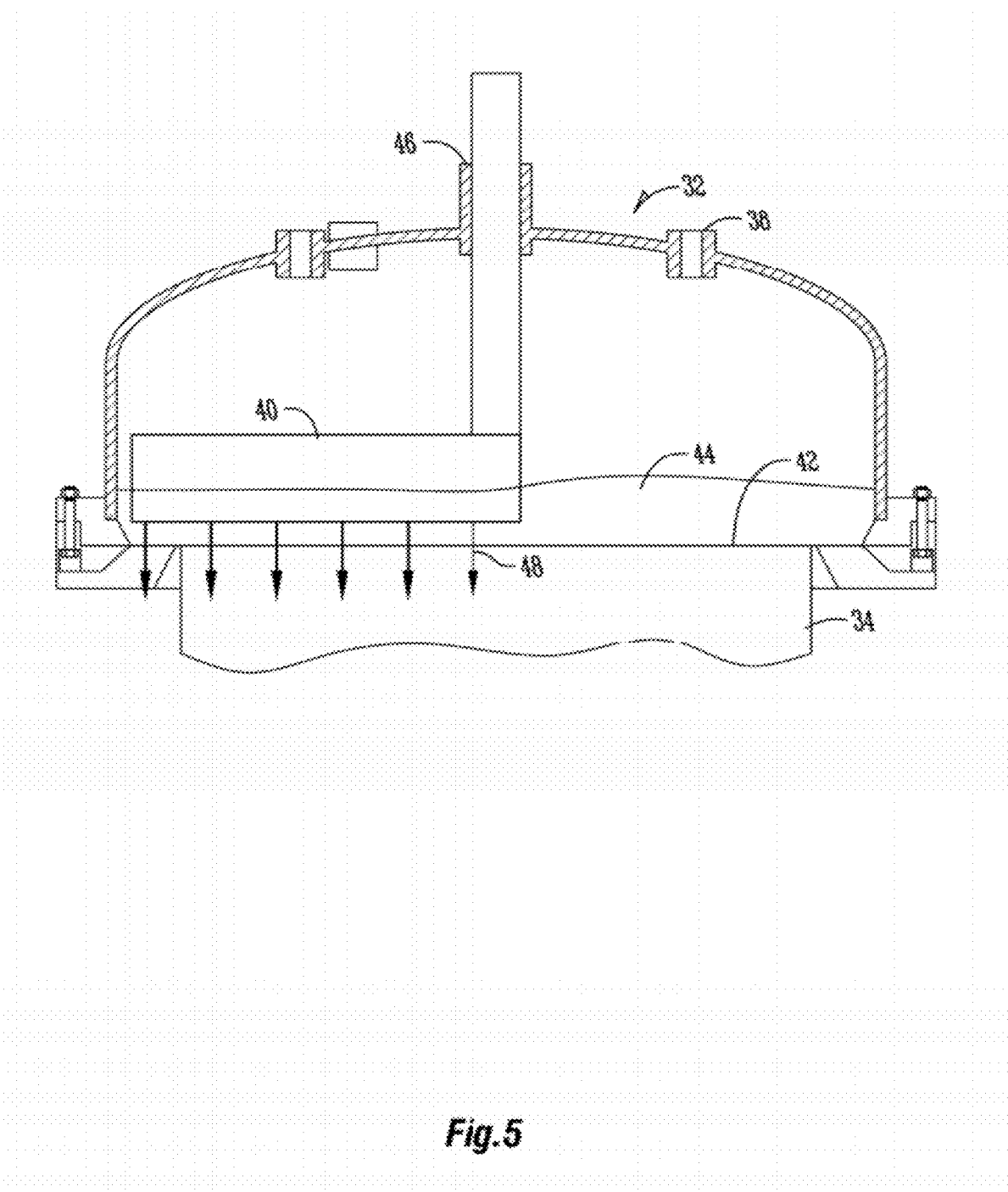
FIG. 5 is a sectional view of a portion of the ultrasound bell jar assembly.

FIG. 5 illustrates that an ultrasonic frequency signal 48 travels through the liquid bath 44 and the pressurized diaphragm 42 and into the test piece 34. The probe 40 which is located inside of the bell-jar assembly 32 is suspended in a bath of liquid 44 which provides the consistent coupling with the top side of the pressurized diaphragm 42. This liquid bath 44 allows the probe 40 to be situated some distance from the diaphragm 42 and gives it the ability to move freely over the surface of the part while maintaining its ultrasonic coupling with the part. All connections to the probe 40 are fed through the center shaft which supports and stabilizes the probe in the bath 44 via a sealed bearing assembly at the top of the bell-jar (probe feed-through 46). Once the part is in place and the bell-jar is pressurized the probe can sweep over the part to acquire the sample. Other inputs into the bell-jar include fluid supply ports, pressure relief ports, and additional ports for sensing and detection devices.

Figure 6:
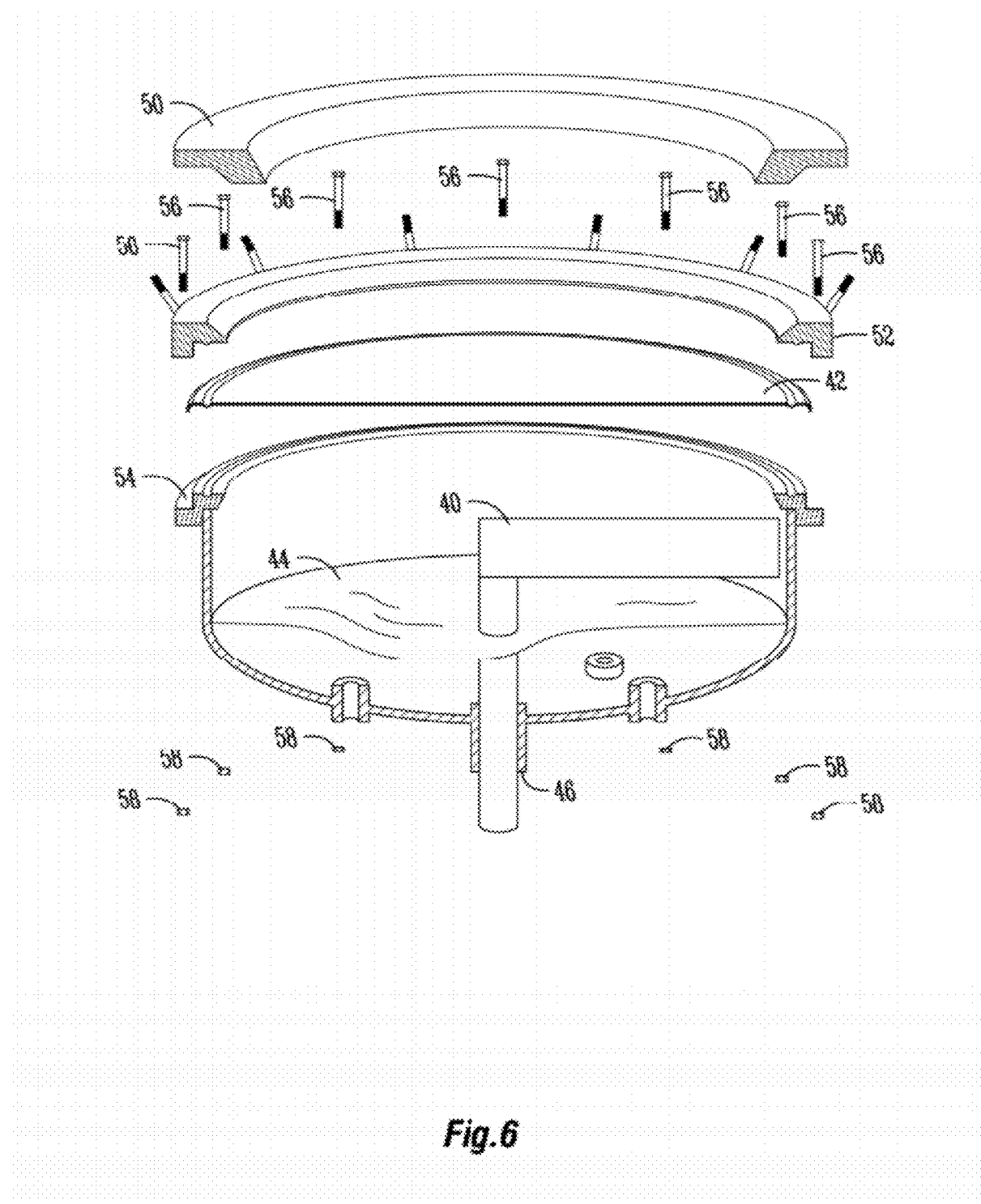
FIG. 6 is an exploded view of a bell-jar shown upside-down in service mode.

FIG. 6 provides an exploded view of the ultrasound bell-jar assembly 32. The assembly 32 includes a secondary backing ring 50 and a main backing ring 52. A clamp ring 54 in conjunction with nuts 58 and bolts 56 is used to secure the diaphragm 42. Servicing the bell-jar and internal components is accomplished by rotating the bell-jar upside-down and removing the flange rings and the diaphragm. The backing rings 50, 52 are placed to clamp the diaphragm 42 in place and to back the diaphragm 42 in locations where the piece is not in contact with the diaphragm 42 to eliminate bulging of the pressurized diaphragm 42 in unsupported regions.

Figure 7:
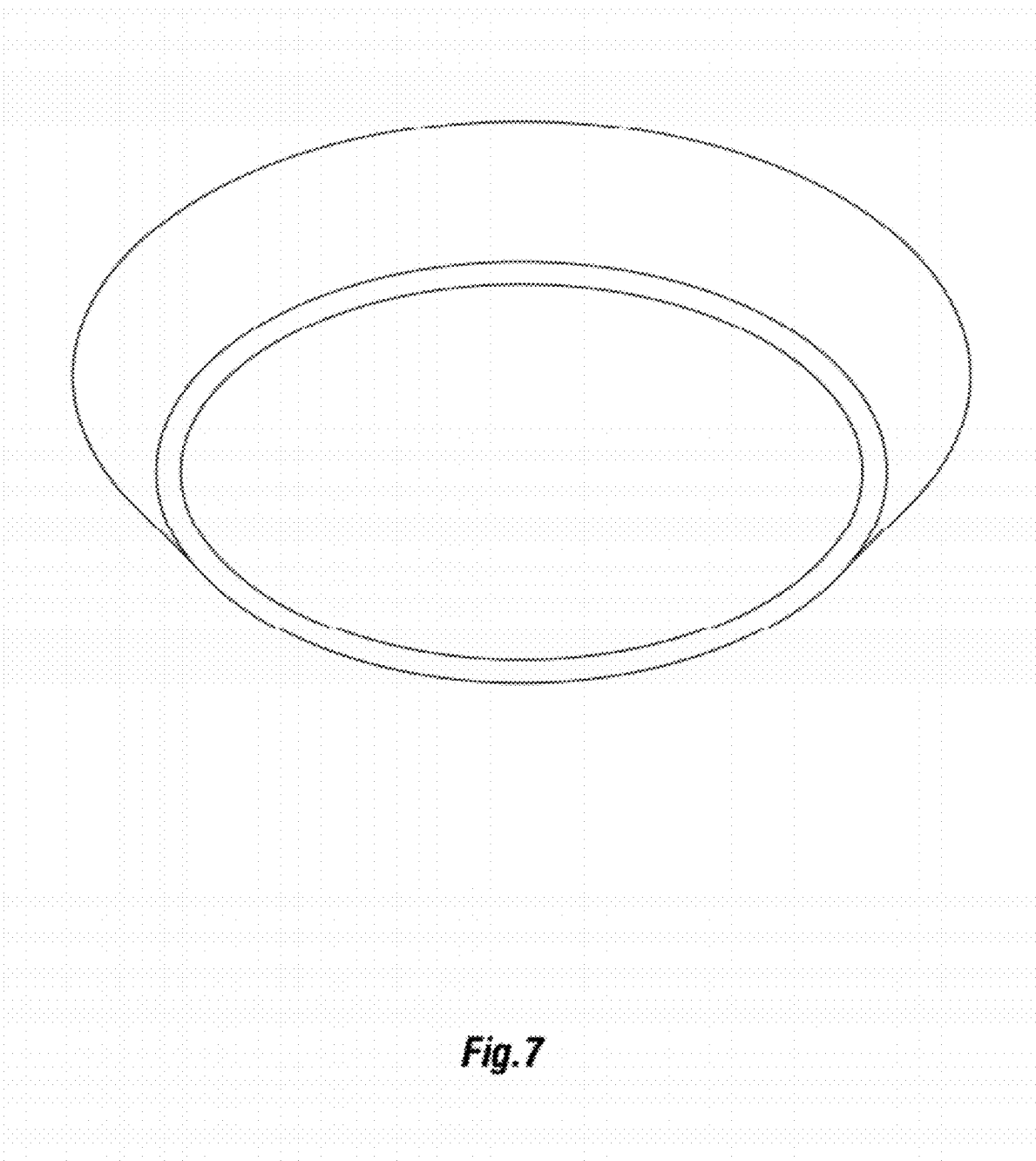
FIG. 7 is an image showing no pressure in the bell-jar on the DPF monolith substrate.
Figure 8:
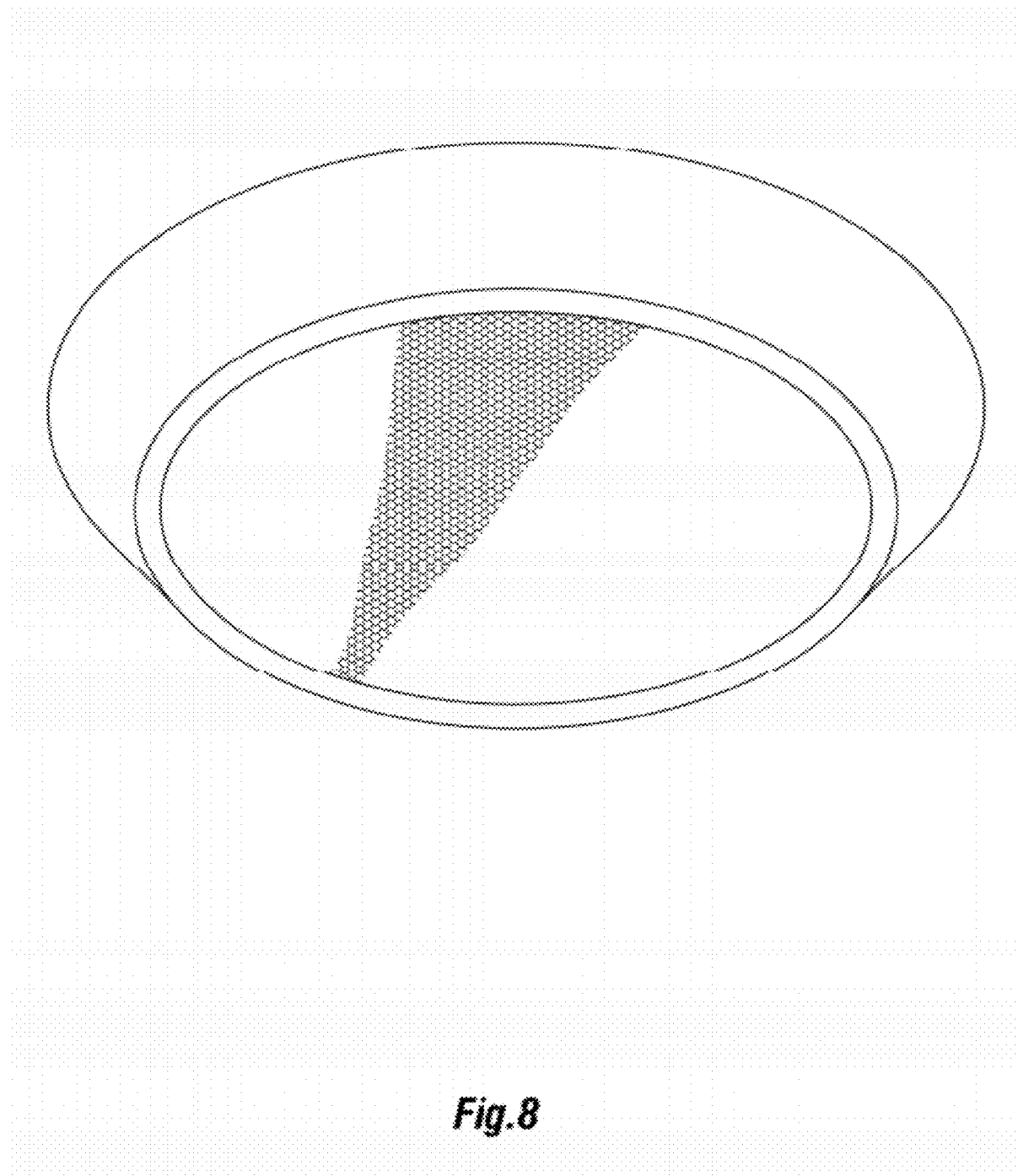
FIG. 8 is an image showing pressure in bell-jar on DPF monolith substrate-notice the cell structure appear.
Figure 9:
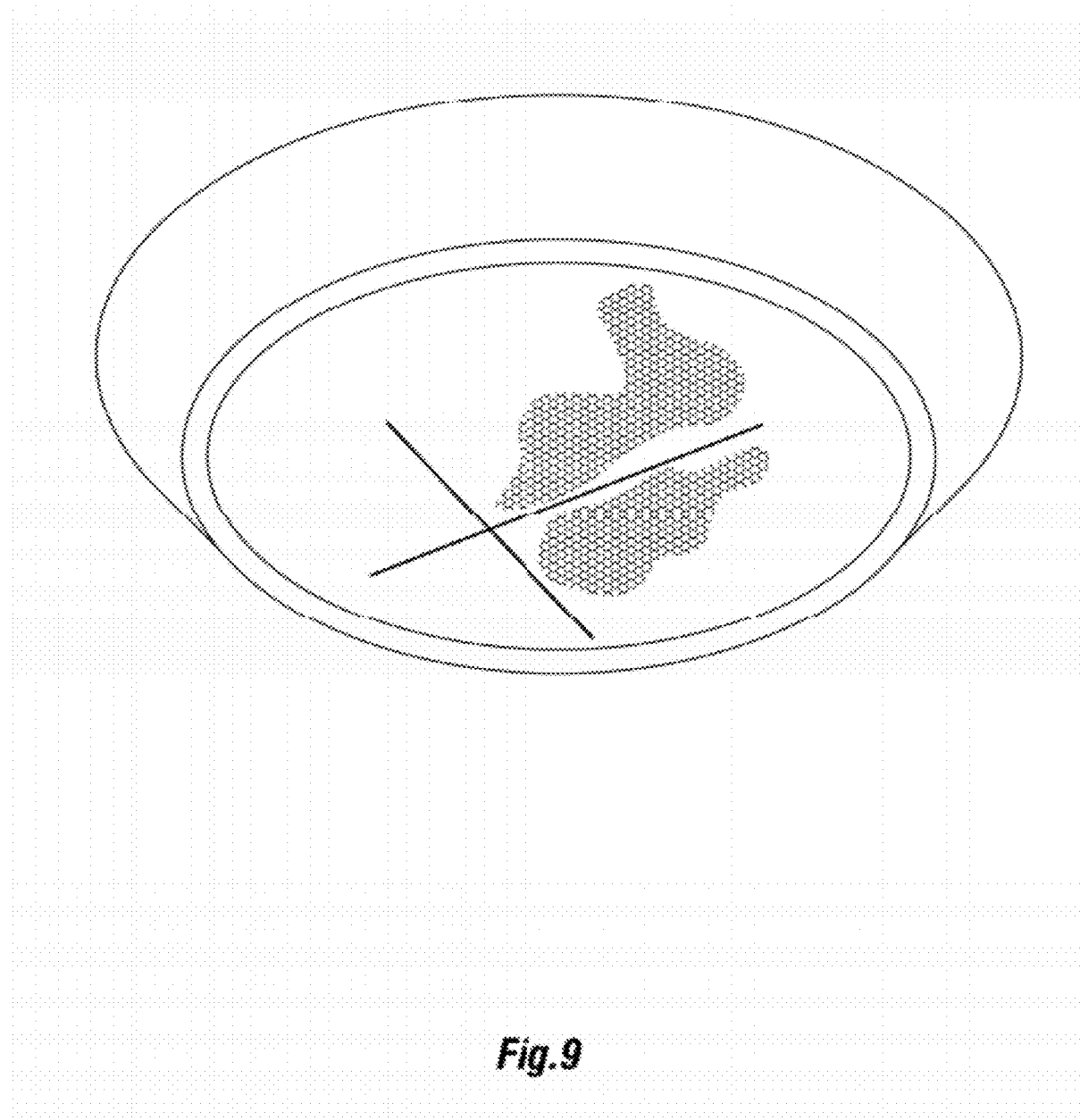
FIG. 9 is an image showing pressure in the bell-jar on segmented substrate-notice the segments and cell structure appear.
Figure 10:
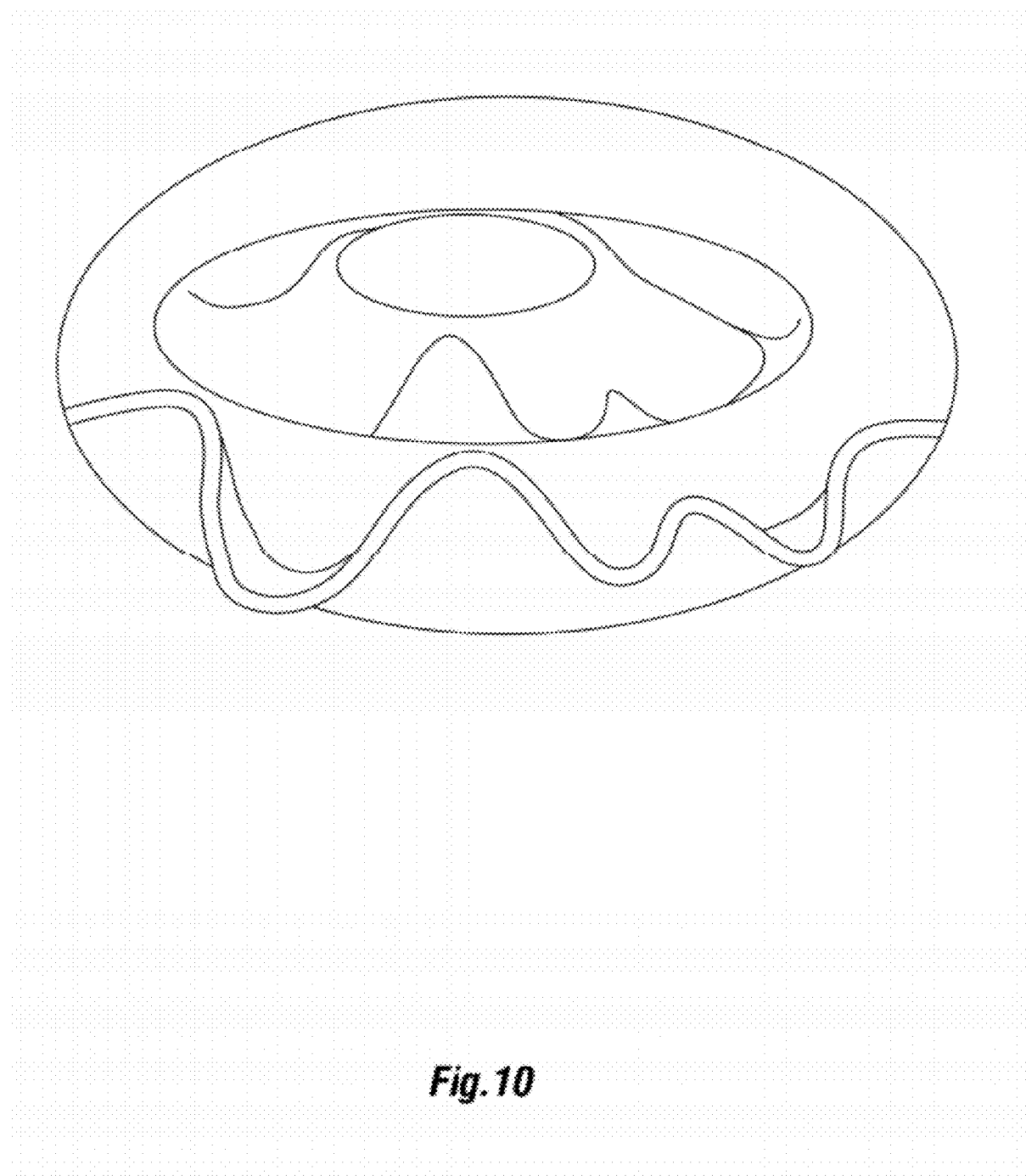
FIG. 10 is an image showing the test bell-jar with water under pressure.

FIG. 7 is a photograph of a bell jar test showing no pressure across the face of the diaphragm. FIG. 8 is a photograph illustrating pressure in pressure vessel on DPF monolith substrate-notice the cell structure showing through the membrane surface. FIG. 9 is a photograph of pressure in the pressure vessel on segmented substrate-notice the segments and cell structure showing through the membrane surface. The pressure vessel may contain a liquid or gel solution which will act in conjunction with the pressurized diaphragm as the final couplant between the Ultrasonic probe and the test piece. FIG. 10 is a photograph illustrating the test pressure vessel with water under pressure.

Figure 11:
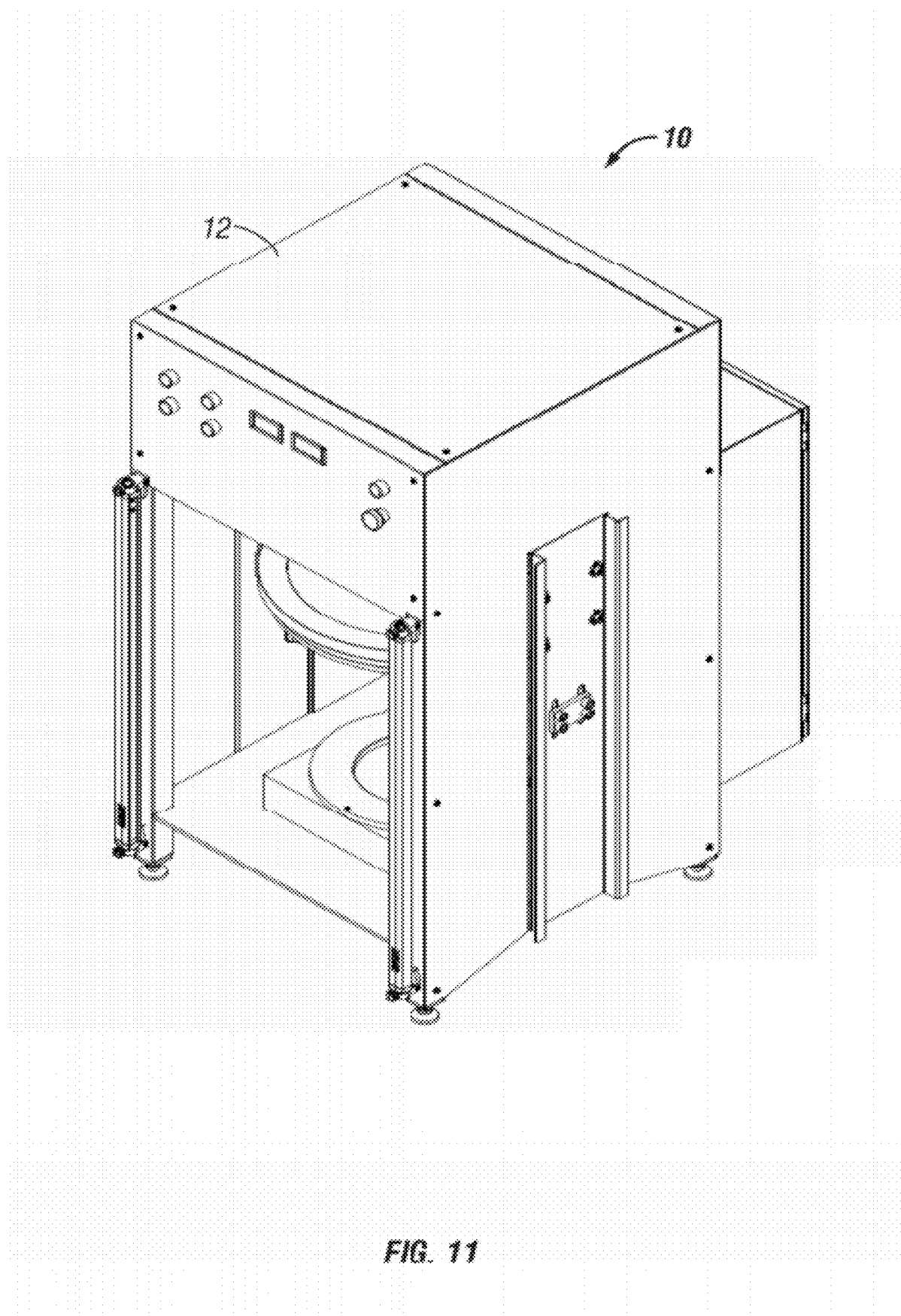
FIG. 11 is a perspective view of one embodiment of an ultrasound test unit
Figure 12:
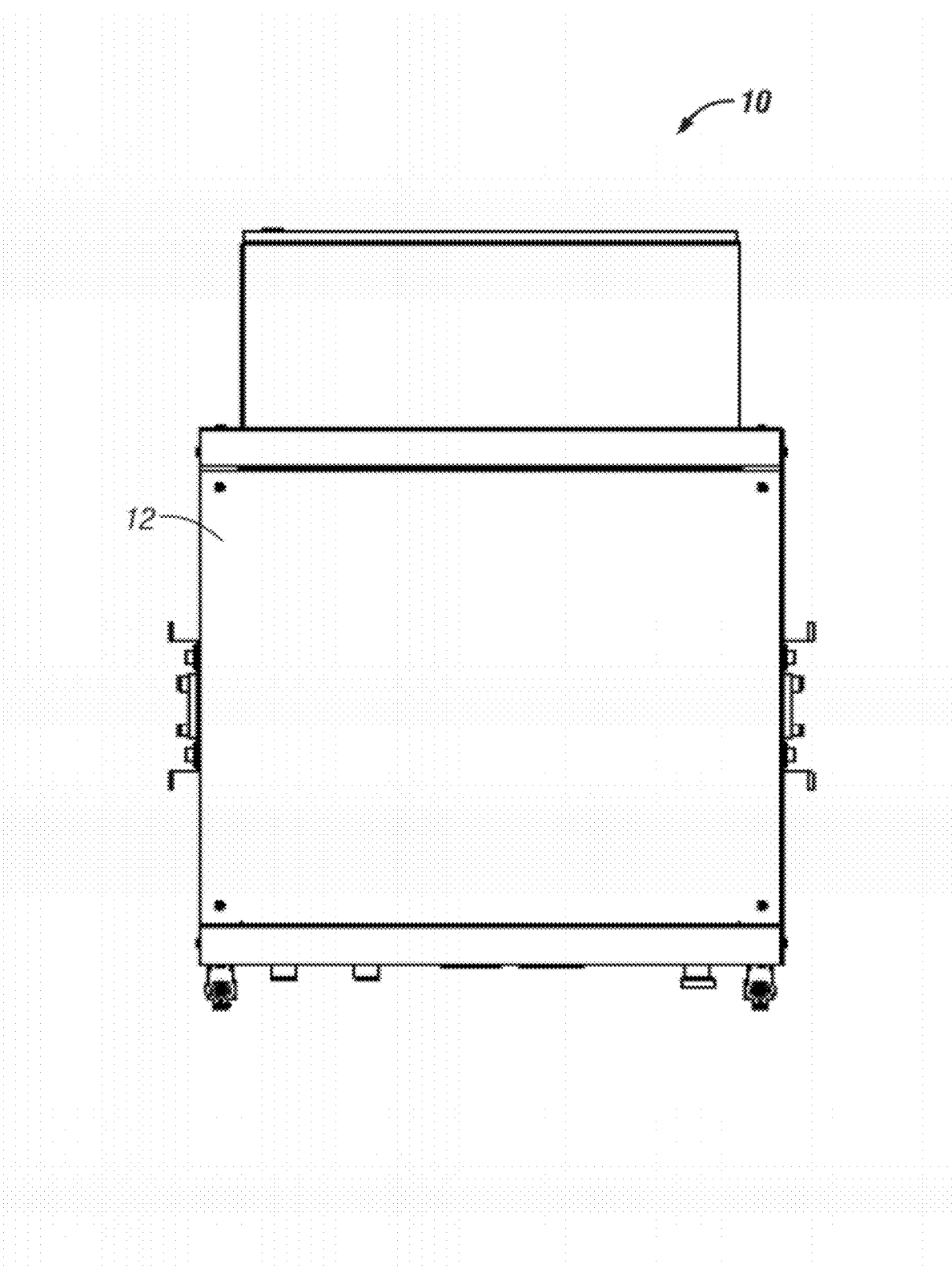
FIG. 12 is a top view of one embodiment of an ultrasound test unit.
Figure 13:
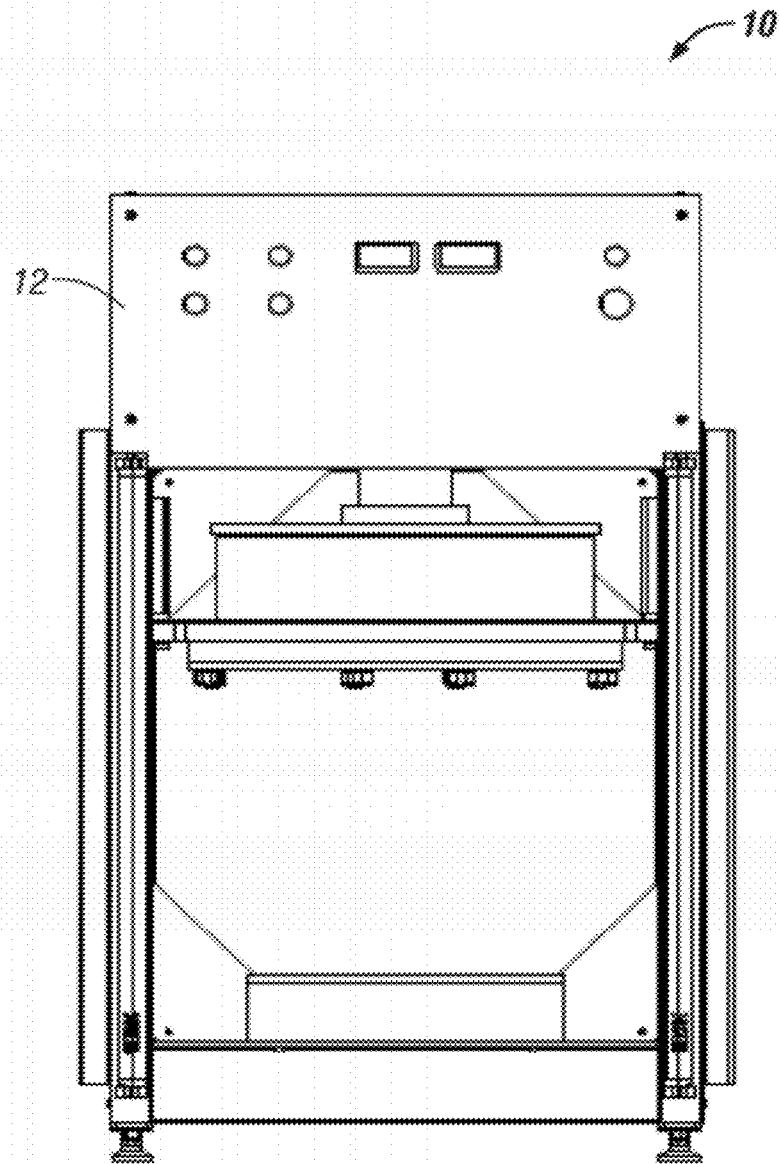
FIG. 13 is a front view of one embodiment of an ultrasound test unit.
Figure 14:
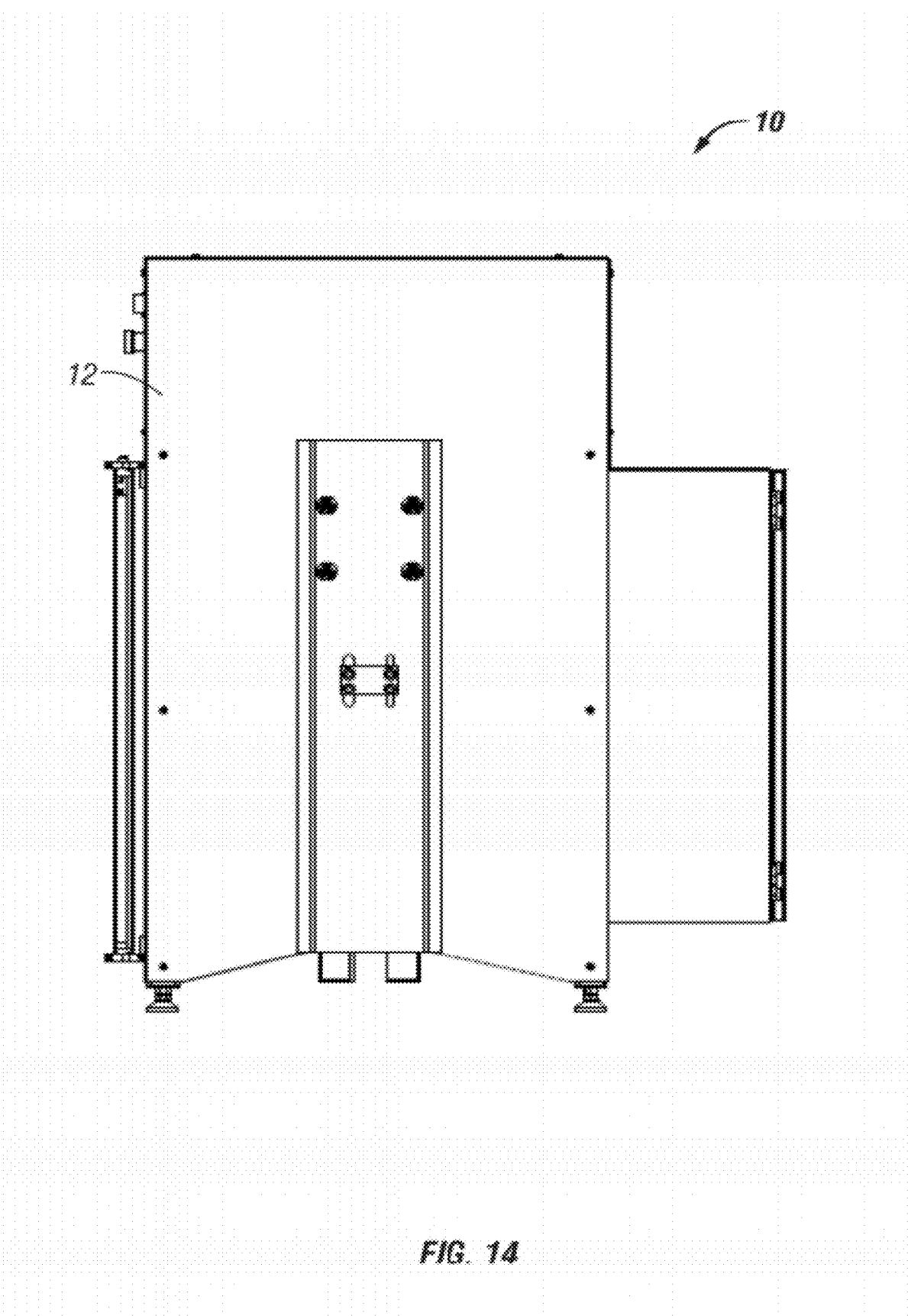
FIG. 14 is a side view of one embodiment of an ultrasound test unit.

FIG. 11 is a perspective view of one embodiment of an ultrasound test unit. The ultrasound test unit 10 has a housing 12. FIG. 12 is a top view of the ultrasound test unit 10. FIG. 13 is a front view of the ultrasound test unit 10. FIG. 14 is a side view of the ultrasound test unit 10.

Figure 15:
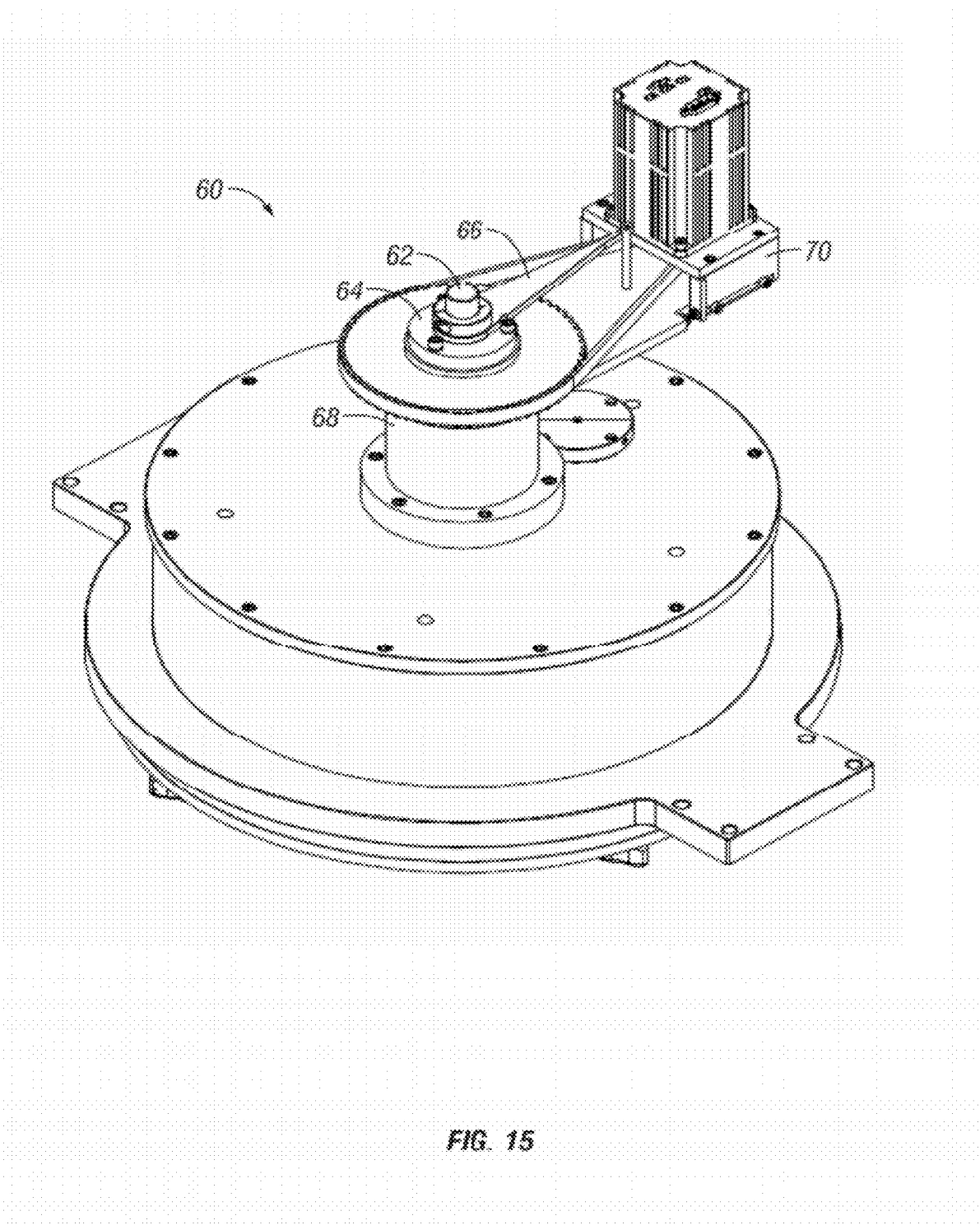
FIG. 15 is a perspective view of one embodiment of a jar assembly.
Figure 16:
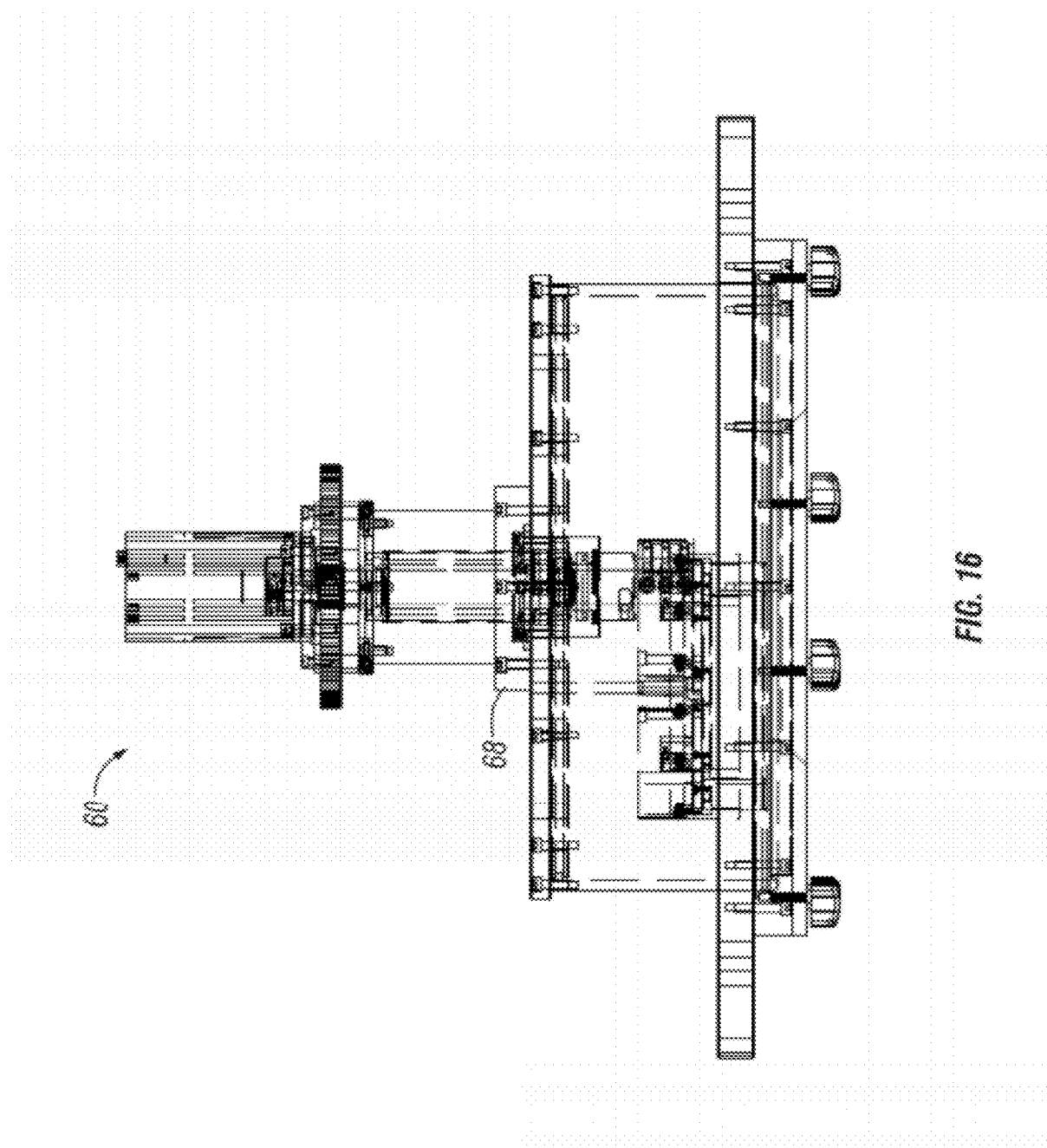
FIG. 16 is a side view of one embodiment of jar assembly.
Figure 17:
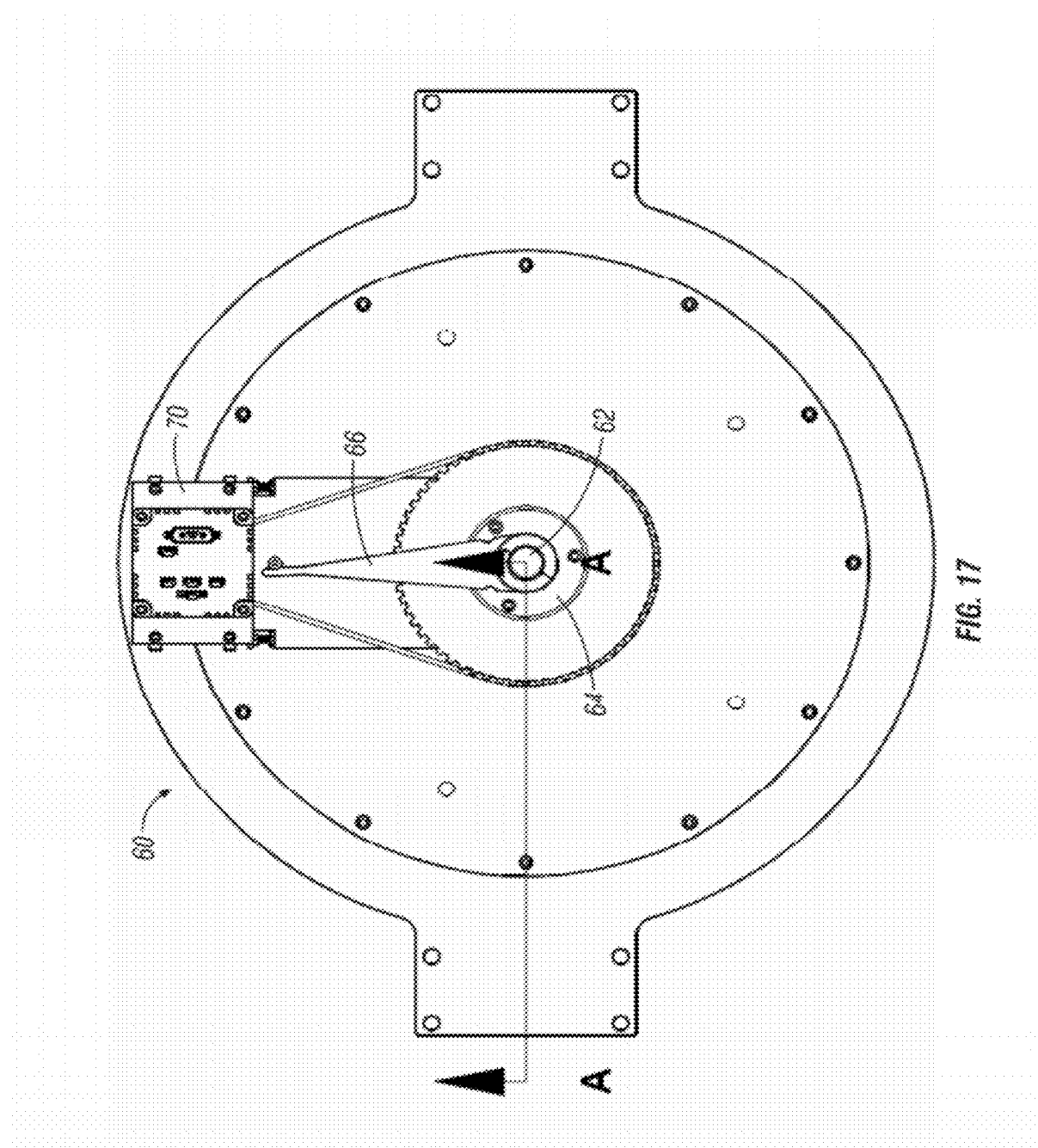
FIG. 17 is a top view of one embodiment of a jar assembly.

FIG. 15 is a perspective view of one embodiment of a jar assembly showing the drive assembly. The assembly 60 includes a drive shaft 62 and a shaft collar 64. A hard stop level 66 is also shown. A motor mount assembly 70 is shown as well as a bearing housing assembly 68. FIG. 16 is a side view of one embodiment of jar assembly. FIG. 17 is a top view of one embodiment of a jar assembly.

Figure 18:
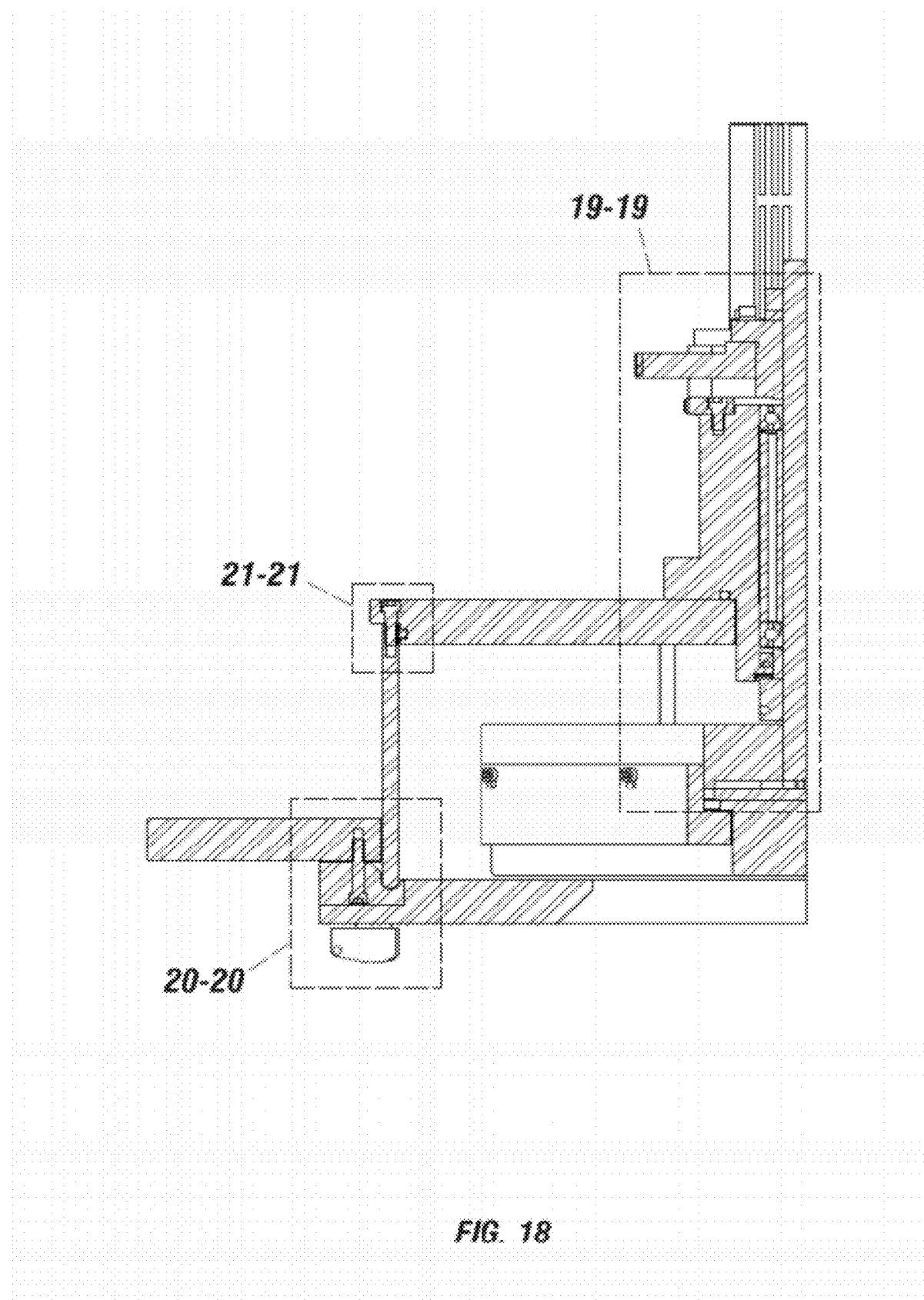
FIG. 18 is a sectional view of one embodiment of a jar assembly taken along line A-A of FIG. 17.
Figure 19:
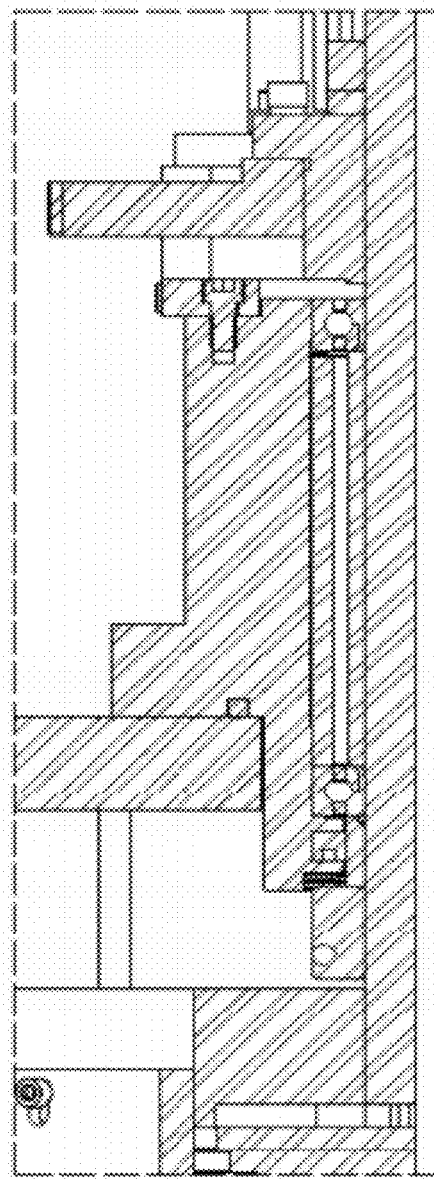
FIG. 19 is a detail view of A of FIG. 18.
Figure 20:
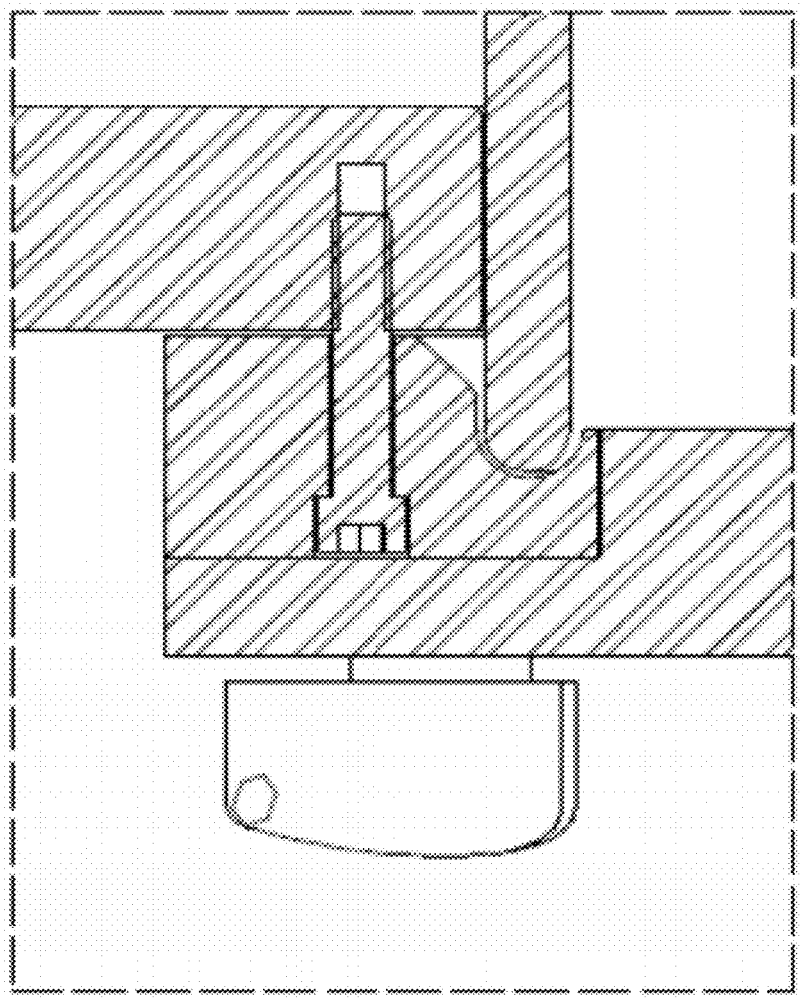
FIG. 20 is a detail view of B of FIG. 18.
Figure 21:
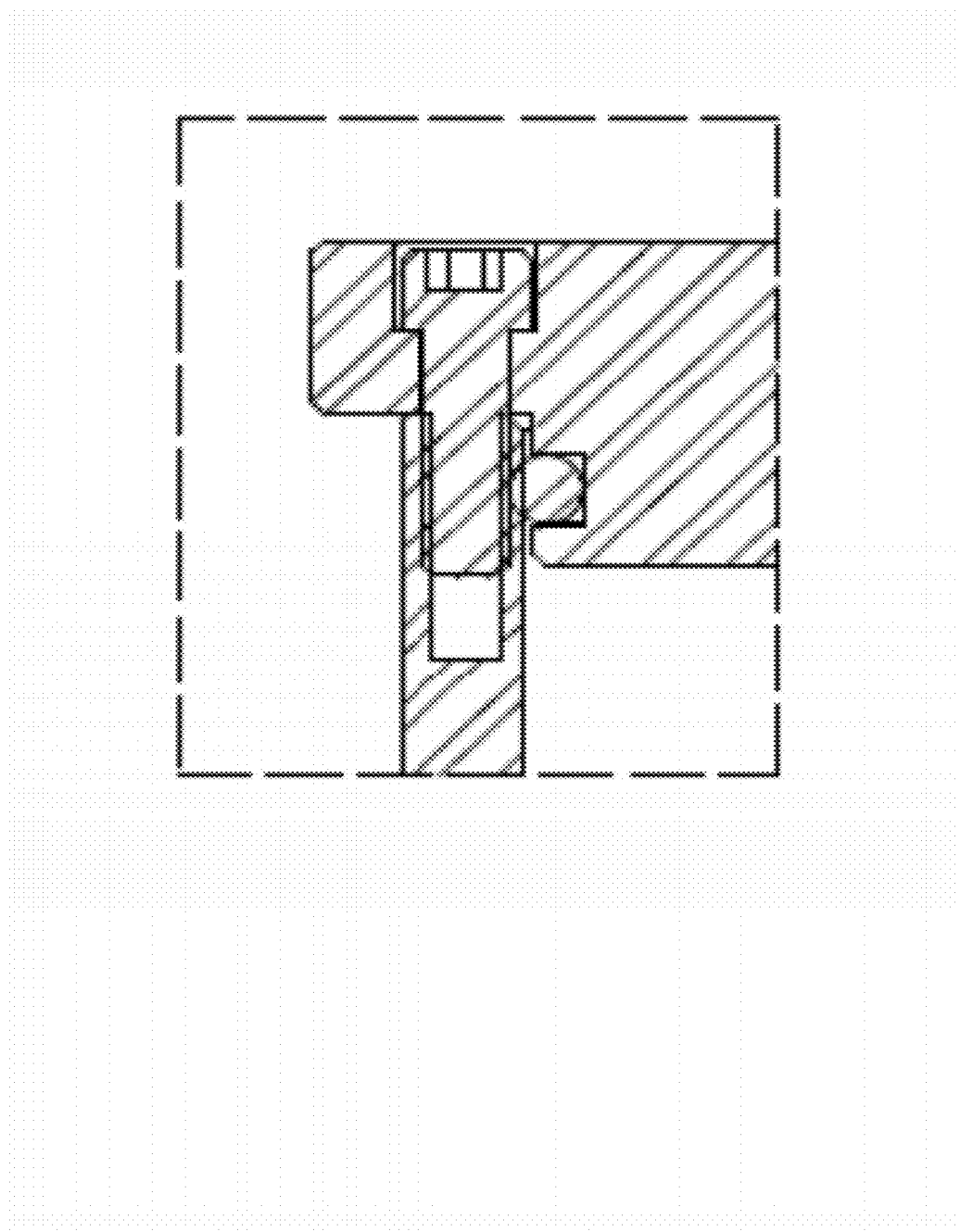
FIG. 21 is a detail view of C of FIG. 18.
Figure 22:
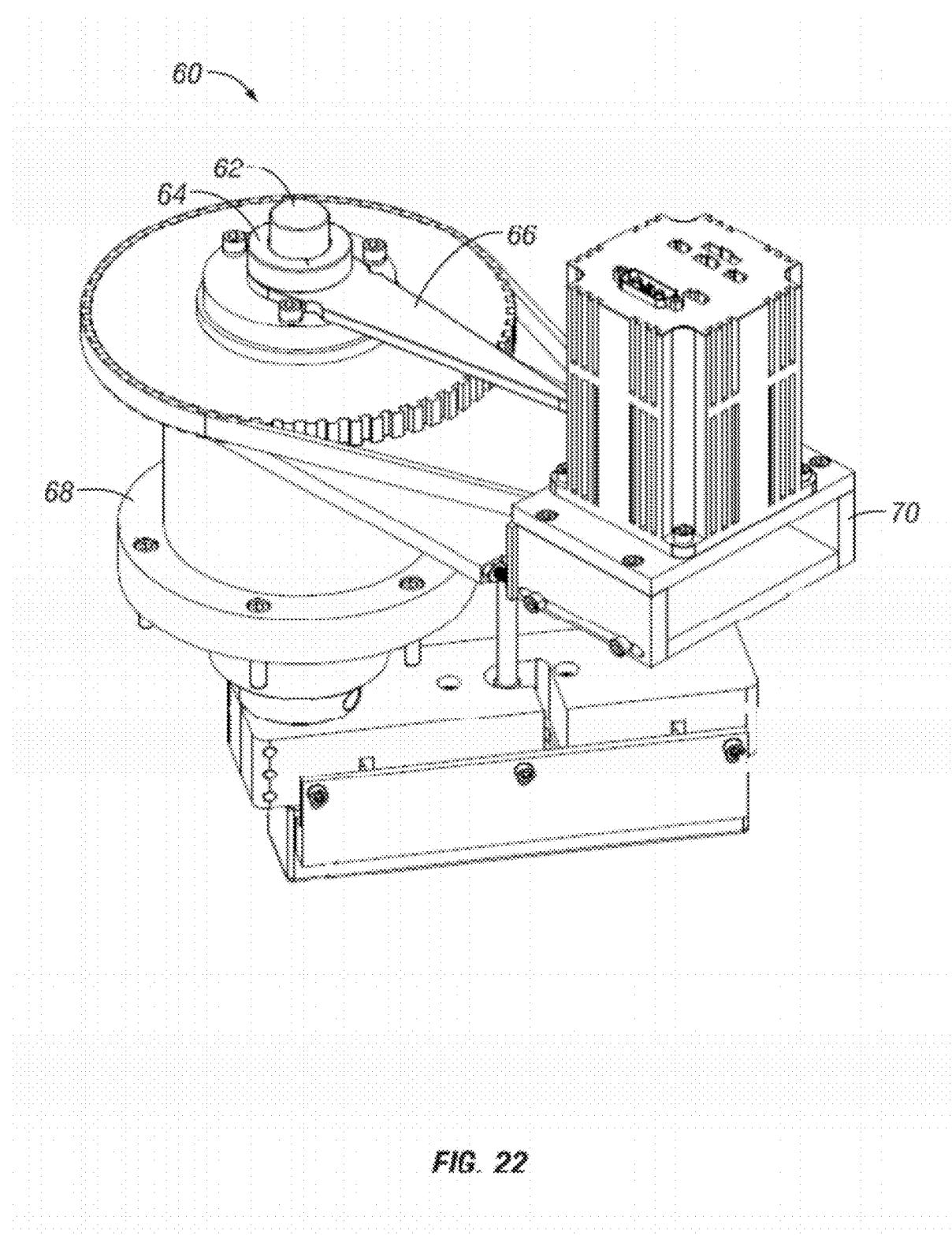
FIG. 22 is a perspective view of one embodiment of a drive assembly.
Figure 23:
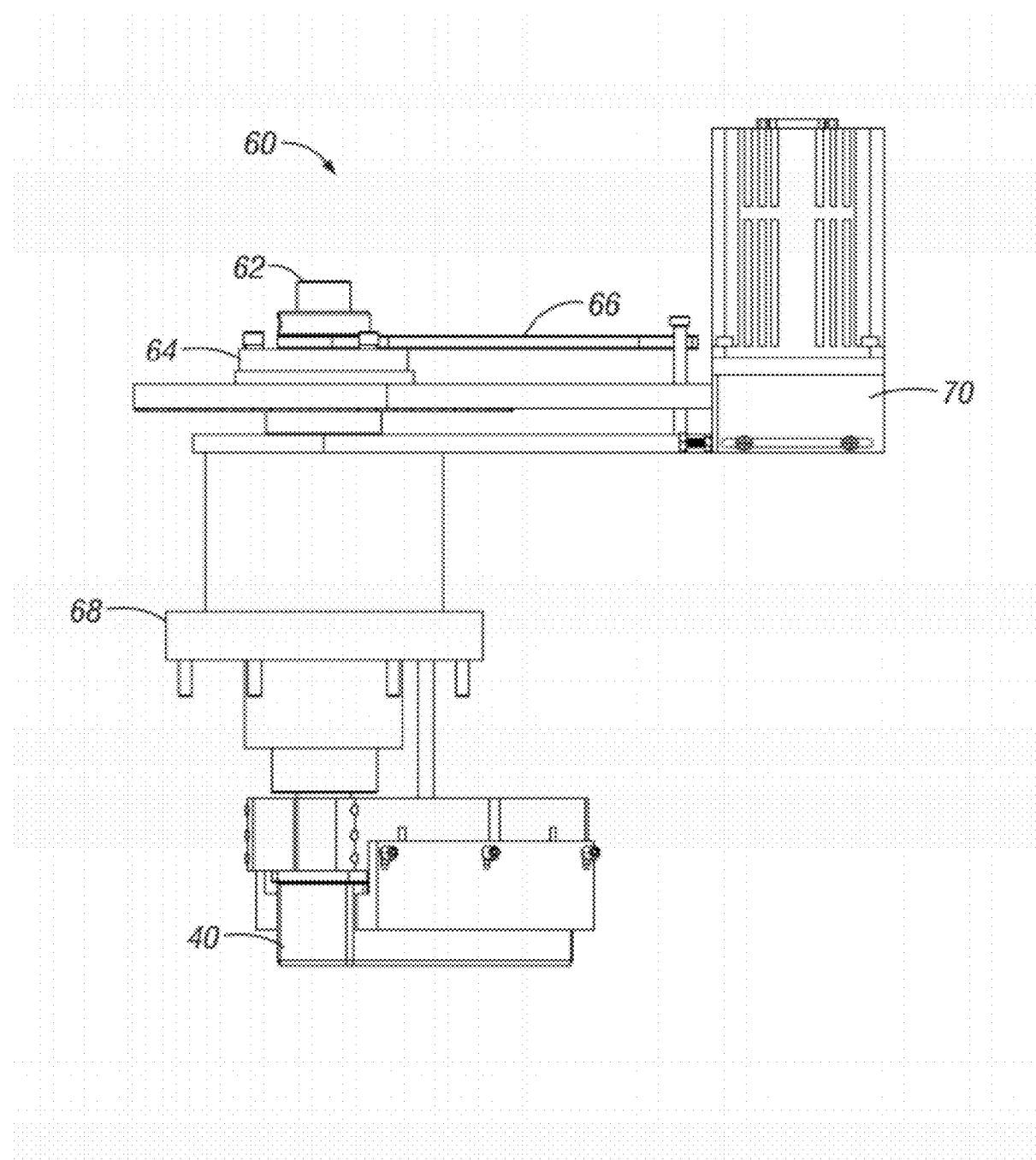
FIG. 23 is a front view of the drive assembly of FIG. 22.
Figure 24:
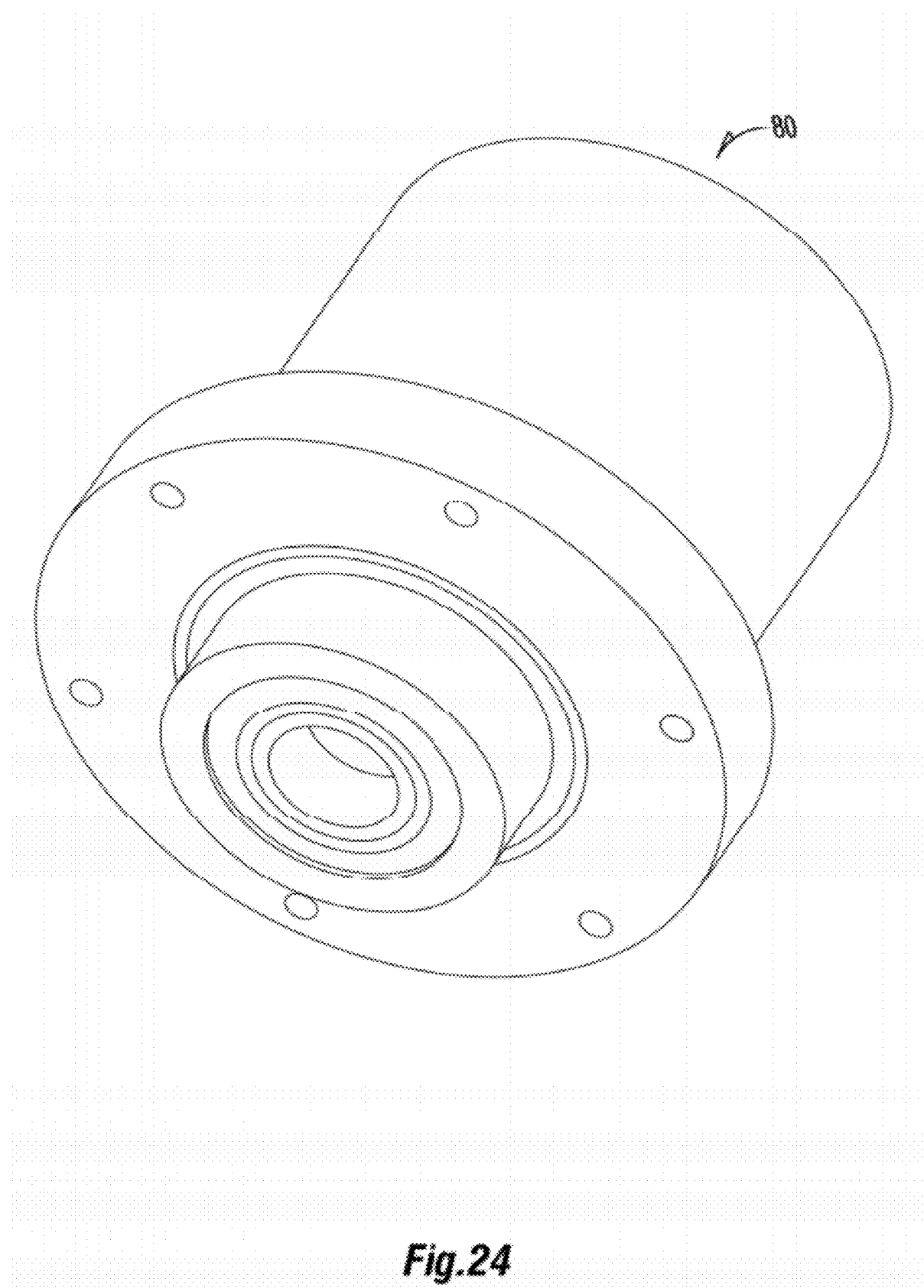
FIG. 24 is a perspective view of one embodiment of a drive assembly bearing housing.

FIG. 18 is a sectional view of one embodiment of a jar assembly taken along line A-A of FIG. 17. FIG. 19 is a detail view of A of FIG. 18. FIG. 20 is a detail view of B of FIG. 18. FIG. 21 is a detail view of C of FIG. 18. FIG. 22 is a perspective view of one embodiment of a drive assembly. FIG. 23 is a front view of the drive assembly of FIG. 22. FIG. 24 is a perspective view of one embodiment of a jar bearing housing.

Figure 25:
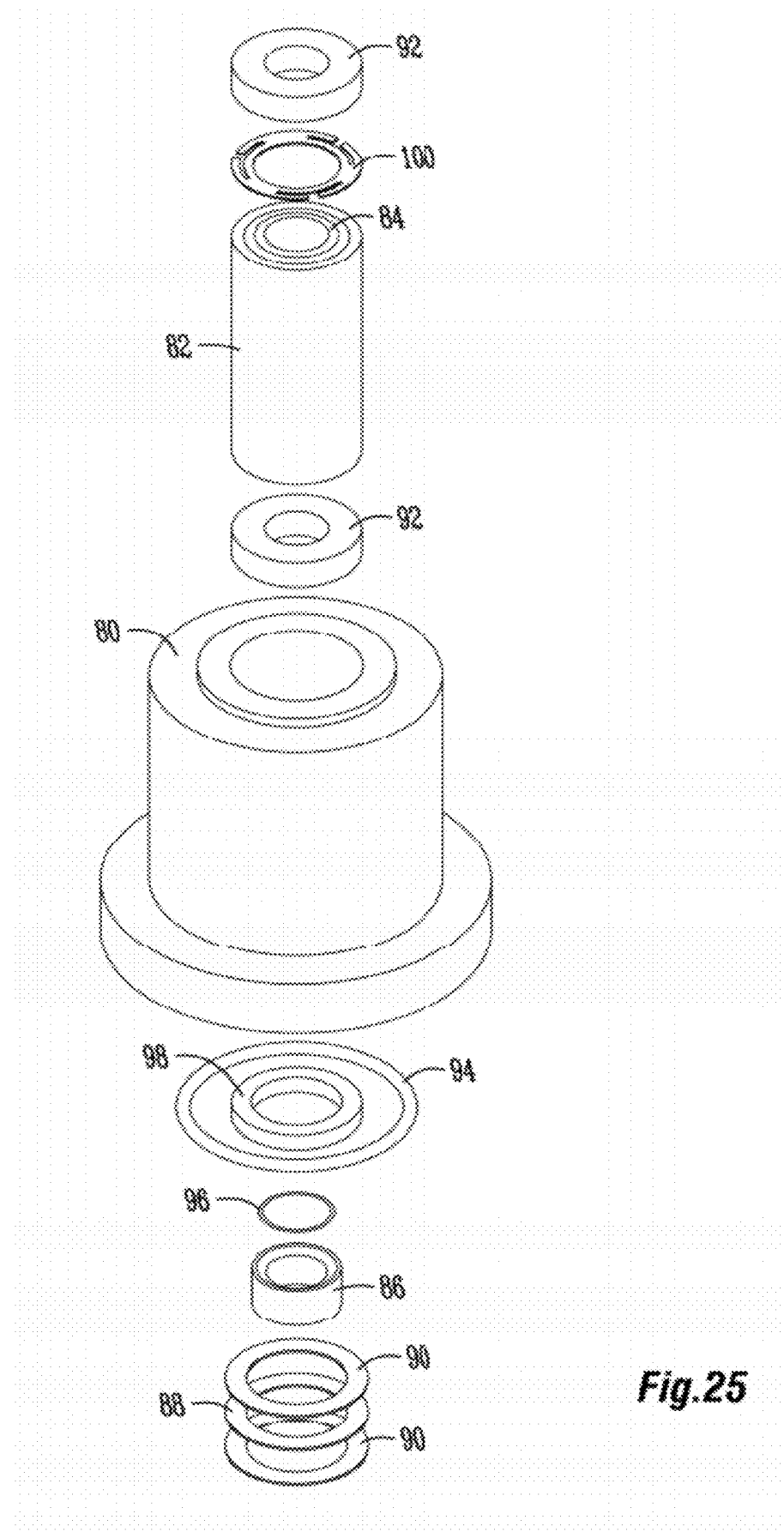
FIG. 25 is an exploded view of one embodiment of a drive assembly bearing housing.

FIG. 25 is an exploded view of one embodiment of a jar bearing housing 80. A bearing housing 80 is shown as well as an outer bearing spacer 82 and an inner bearing spacer 84. There is a lower bearing spacer 86. A thrust bearing 88 is shown as well as thrust washers 90. A shielded ball bearing 92 is shown as well as round O-ring 94 and a second round O-ring 96. A U-cup seal 98 is shown as well as a finger disk spring 100.

The present invention contemplates numerous variations, options, and alternatives. For example, the jar assembly need not be a jar but may be another form of a pressure vessel or container. The liquid bath may be of any number of types of liquids. Any number of drive mechanisms may be used. These and other variations, options, and alternatives are within the spirit and scope of the invention.

What is claimed is:

1. A method for ultrasonic testing, comprising:
   placing an ultrasonic probe in a liquid bath inside of a pressure vessel having a nonpermeable elastomeric diaphragm stretched across an opening of the pressure vessel such that the ultrasonic probe is suspended over the diaphragm with liquid between the ultrasonic probe and the diaphragm;
   wherein the ultrasonic probe is placed inside the pressure vessel through a probe feed-through opening comprising a sealed bearing assembly to allow for electrical connections to the probe to be passed into the pressure vessel while maintaining pressure;
   positioning a test piece proximate or adjacent to the elastomeric diaphragm, wherein the step of positioning comprises using a stable lift platform which lifts the test piece into the diaphragm of the pressure vessel;
   applying pressure within the pressure vessel to bring the elastomeric diaphragm towards the test piece;
   conducting ultrasonic testing of the test piece using the ultrasonic probe.

2. The method of claim 1 wherein the pressure vessel is a bell-jar.

3. The method of claim 1 wherein the test piece is a catalyst substrate.

4. The method of claim 1 wherein the test piece is a ceramic material.

5. The method of claim 1 wherein the step of applying pressure within the container forces the elastomeric diaphragm against a surface of the test piece thereby conforming the elastomeric diaphragm to the surface of the test piece to provide intimate contact.

6. The method of claim 1 wherein the liquid bath comprises a gel solution.

7. The method of claim 1 wherein the pressure is within the range of about 1 pound per square inch to about 15 pounds per square inch.

8. The method of claim 1 wherein the step of conducting ultrasonic testing of the test piece using the ultrasonic probe comprises moving the probe within the pressure vessel in a rotational or linear fashion.

9. The method of claim 1 further comprising rejecting the test piece based on the ultrasonic testing.

10. The method of claim 1, further comprising a mechanism for holding the ultrasonic probe in a static location.

11. An apparatus for ultrasonic testing of a test piece, comprising:
    a pressure vessel having a nonpermeable elastomeric diaphragm and configured to contain a liquid bath; and
    an ultrasonic probe disposed within the pressure vessel;
    wherein the ultrasonic probe is suspended over the diaphragm to allow liquid to flow between the ultrasonic probe and the diaphragm;
    a stable lift platform for lifting the test piece proximate or adjacent to the elastomeric diaphragm; and
    a probe feed-through opening, comprising a sealed bearing assembly, to allow for electrical connections to the probe to be passed into the pressure vessel while maintaining pressure.

12. The apparatus of claim 11 further comprising a drive shaft operatively connected to the pressure vessel for moving the ultrasonic probe in a rotational or linear fashion.

13. The apparatus of claim 12 further comprising a drive mechanism operatively connected to the drive shaft.

14. The apparatus of claim 11 further comprising a pressure inlet to the pressure vessel for increasing pressure within the pressure vessel.

15. The apparatus of claim 11, further comprising a mechanism for holding the ultrasonic probe in a static location.

16. The apparatus of claim 11, further comprising other inputs into the pressure vessel including fluid supply ports, pressure relief ports, and additional ports for sensing and detection devices.

17. The apparatus of claim 11, wherein the pressure vessel comprises a secondary backing ring and a main backing ring.

18. The apparatus of claim 17, wherein the backing rings are placed to clamp the diaphragm in place and to back the diaphragm in locations where the piece is not in contact with the diaphragm to eliminate bulging of the pressurized diaphragm in unsupported regions.

19. The apparatus of claim 17, wherein nuts and bolts are used to secure the diaphragm.

20. An apparatus for ultrasonic testing of a test piece, comprising:
    a bell jar;
    a liquid bath comprising a gel, the liquid bath contained within the bell jar;
    a nonpermeable elastomeric diaphragm stretched across an opening of the bell jar;
    an ultrasonic probe positioned above the elastomeric diaphragm and separated from the elastomeric diaphragm to allow liquid from the liquid bath to flow between the ultrasonic probe and the diaphragm;
    a probe feed-through opening comprising a sealed bearing assembly to allow for electrical connections to the probe to be passed into the bell jar while maintaining pressure;
    a drive shaft operatively connected to the bell jar for moving the ultrasonic probe in a rotational or linear fashion;
    a drive mechanism operatively connected to the drive shaft;
    a stable lift platform for lifting a test piece proximate or adjacent to the elastomeric diaphragm; and
    a mechanism for optionally holding the ultrasonic probe in a static location.

21. The apparatus of claim 20, wherein the bell jar comprises a secondary backing ring and a main backing ring.

22. The apparatus of claim 21, wherein the backing rings are placed to clamp the diaphragm in place and to back the diaphragm in locations where the piece is not in contact with the diaphragm to eliminate bulging of the pressurized diaphragm in unsupported regions.

23. The apparatus of claim 21, wherein nuts and bolts are used to secure the diaphragm.

* * * * *